United States Patent
Nair et al.

(10) Patent No.: US 7,887,685 B2
(45) Date of Patent: Feb. 15, 2011

(54) MULTILAYER GAS SENSOR HAVING DUAL HEATING ZONES

(75) Inventors: Balakrishnan G. Nair, Sandy, UT (US); Jesse Alan Nachlas, Prescott, AZ (US)

(73) Assignee: Caterpillar Inc., Peoria, IL (US)

( * ) Notice: Subject to any disclaimer, the term of this patent is extended or adjusted under 35 U.S.C. 154(b) by 554 days.

(21) Appl. No.: 11/980,611

(22) Filed: Oct. 31, 2007

(65) Prior Publication Data

US 2008/0210576 A1 Sep. 4, 2008

Related U.S. Application Data

(63) Continuation-in-part of application No. 11/182,278, filed on Jul. 14, 2005, now Pat. No. 7,611,612.

(51) Int. Cl.
*G01N 27/407* (2006.01)

(52) U.S. Cl. .................... 204/426; 205/785.5; 205/785; 205/780.5

(58) Field of Classification Search ................. 204/408, 204/410, 411, 421–429, 431; 205/780.5, 205/781, 783.5–785, 785.5, 787; 219/201–208, 219/482–506; 73/23.31, 23.32
See application file for complete search history.

(56) References Cited

U.S. PATENT DOCUMENTS

| 4,300,990 | A | * | 11/1981 | Maurer ...................... 204/412 |
|---|---|---|---|---|
| 4,668,374 | A | | 5/1987 | Bhagat et al. |
| 4,786,399 | A | | 11/1988 | Wertheimer et al. |
| 4,818,363 | A | | 4/1989 | Bayha et al. |
| 4,900,425 | A | | 2/1990 | Sasayama et al. |
| 5,288,389 | A | * | 2/1994 | Yamada et al. ............... 204/425 |
| 5,389,218 | A | * | 2/1995 | Bonne et al. ................. 205/785 |
| 5,403,452 | A | | 4/1995 | Hielscher et al. |
| 5,470,756 | A | * | 11/1995 | Coles et al. .................. 436/144 |
| 5,602,325 | A | | 2/1997 | McClanahan et al. |
| 5,696,313 | A | * | 12/1997 | Hafele ........................ 73/23.31 |
| 5,989,398 | A | * | 11/1999 | Young et al. ................. 204/424 |
| 6,270,638 | B1 | | 8/2001 | Kaneko |
| 6,276,192 | B1 | * | 8/2001 | Sim et al. ................... 73/25.01 |
| 6,287,439 | B1 | * | 9/2001 | Kato et al. ................... 204/425 |
| 6,314,789 | B1 | | 11/2001 | Peter |
| 6,319,377 | B1 | | 11/2001 | Hasei et al. |
| 6,347,543 | B1 | | 2/2002 | Geier et al. |
| 6,408,680 | B2 | | 6/2002 | Friese et al. |
| 6,510,728 | B2 | | 1/2003 | Matsuo et al. |

(Continued)

FOREIGN PATENT DOCUMENTS

DE  3802051  8/1988

(Continued)

*Primary Examiner*—Alexa D Neckel
*Assistant Examiner*—Jennifer Dieterle
(74) *Attorney, Agent, or Firm*—Finnegan, Henderson, Farabow, Garrett & Dunner LLP

(57) ABSTRACT

A gas sensor for detecting $NO_X$ is provided. The gas sensor may have a plurality of substrate members, a first sensing electrode, and a second sensing electrode. The gas sensor may also have a first heater element associated with the first sensing electrode and being located on a first side of one of the plurality of substrate members, and a second heater element associated with the second sensing electrode and being located on a second opposing side of the one of the plurality of substrate members.

21 Claims, 3 Drawing Sheets

U.S. PATENT DOCUMENTS

| | | |
|---|---|---|
| 6,537,431 B1 | 3/2003 | Tatsumoto et al. |
| 6,797,138 B1 | 9/2004 | Detwiler et al. |
| 6,940,287 B2 | 9/2005 | Weyl et al. |
| 7,163,609 B2 | 1/2007 | Ando et al. |
| 7,611,612 B2 * | 11/2009 | Nair et al. ................ 204/426 |
| 2002/0073765 A1 * | 6/2002 | Kikuchi et al. ............ 73/25.01 |
| 2005/0006236 A1 | 1/2005 | Kim et al. |
| 2007/0012566 A1 | 1/2007 | Nair et al. |
| 2007/0051641 A1 | 3/2007 | Kroot et al. |

FOREIGN PATENT DOCUMENTS

| | | |
|---|---|---|
| DE | 4240812 | 6/1994 |
| GB | 2046921 | 11/1980 |

* cited by examiner

MULTILAYER GAS SENSOR HAVING DUAL HEATING ZONES

RELATED APPLICATIONS

This application is a Continuation In Part Application of U.S. patent application Ser. No.: 11/182,278, of Balakrishnan G. Nair and Jesse Nachlas filed Jul. 14, 2005 now U.S. Pat. No. 7,611,612 and entitled "Multilayer Ceramic $NO_X$ Gas Sensor Device." application Ser. No. 11/182,278 is incorporated herein by reference in its entirety.

US GOVERNMENT RIGHTS

This invention was made in part with government support under Grant Numbers 68-D-02-076 and 68-D-03-061 awarded by the United States Environmental Protection Agency. The Government may have certain rights in the invention.

TECHNICAL FIELD

The present disclosure relates generally to a sensor, and more particularly, to a multilayer gas sensor having dual heating zones.

BACKGROUND

The composition of exhaust gases produced by the combustion of hydrocarbon fuels is a complex mixture of oxide gases (NOX, $SO_X$, $CO_2$, CO, $H_2O$), unburned hydrocarbon gases, and oxygen. Measurement of the concentration of these individual exhaust gas constituents in real time can result in improved combustion efficiency and lower emissions of polluting gases. In some cases, the concentration of one gas may influence or control the concentration of a second gas. In these situations, it may be required to know the concentration of the first gas in order to measure the concentration of a second, or even a third gas accurately. Various devices have been proposed to operate as exhaust gas sensors that have the capability of measuring the gas concentration of two or more gases in an exhaust stream.

One gas sensor known in the art is configured as a flat plate multilayer ceramic package designed to include two or more chambers. The first chamber has electrodes attached to an oxygen ion-conducting electrolyte membrane to form an oxygen pump for removing oxygen from a flow of gas entering the sensor. The first chamber also catalyzes the decomposition of $NO_2$ to NO and one-half $O_2$. The oxygen pump in the first chamber also removes the oxygen formed by this process. Thus, in theory, the only oxygen-containing gas that enters the second chamber is NO. The second chamber includes an NO decomposing element that removes the oxygen from the NO using a second oxygen pump. The electrical current produced by the transport of oxygen from the decomposition of NO in the second chamber is correlated to the concentration of NO in the exhaust flow.

A number of concerns affect the commercial application of this known gas sensor. For example, when the $NO_X$ concentration in the exhaust flow is low, residual oxygen can cause significant interference. In addition to the above, the signal current produced by the sensor is very small, thus making it susceptible to interference from the electronic noise commonly found in an automobile. Also, the flow of exhaust gas monitored by such sensors typically has pulsations in its flow rate caused at least in part by engine cylinder firings. These pulsations impair the ability of the oxygen pump to effectively remove all of the free oxygen and may result in measurement error. The gas sensor may also contain a small diffusion aperture used to limit the passage of gas into the measurement chambers. The small diffusion aperture has been demonstrated to clog during use.

Another known gas sensor utilizes a similar flat plate multilayer ceramic package design, but is a mixed potential-type sensor rather than an amperometric-type sensor, and the first chamber is used to convert NO to $NO_2$ and vice versa. It is well established that in mixed potential $NO_X$ sensors, the voltage signals generated from the gas species NO and $NO_2$ are of opposite sign. As a result, it is difficult to distinguish a meaningful voltage signal when both gases are present since cancellation may occur.

Some sensor designs have attempted to address this problem by utilizing a flat plate multilayer package design with two separate chambers built into the sensor. Attempts have also been made to convert all of the $NO_X$ gas species into a single species with the use of an electrochemical oxygen pump that pumps oxygen into the first chamber to attempt to convert all of the gas to $NO_2$. Other efforts conversely attempt to remove oxygen from the chamber and reduce all of the $NO_2$ to NO. This "conditioned" gas then passes into the second chamber where the $NO_X$ concentration is measured by the voltage signal generated from a mixed potential type sensor.

There are a number of limitations to this approach that have hampered the commercialization of this configuration. One significant concern is the reproducibility of the conversion system to completely convert all the $NO_X$ gases into a single species under varying gas concentration conditions. In addition, the oxygen pump conversion cell tends to degrade with time, further contributing to the issue of reproducibility. Because the effects of these concerns are magnified in the low concentration range, this measurement approach is not well suited for detecting low concentrations of $NO_X$ gases.

Additional drawbacks common to both of the sensor mechanisms discussed above stem from the fundamental design of the flat plate ceramic multilayer system. Response times tend to be slow because of the complexity of the device requiring gas to first enter through a diffusion port, be conditioned in a first chamber, and then to diffuse into a second chamber. Achieving rapid gas exchange that can keep up with the dynamic environment of an engine's exhaust is difficult in these configurations. Also, the corrosive nature of the gas itself and the fact that it bears fine particulates may result in the clogging of the diffusion controlling port, or at the very least, changes in the gas flow dynamics with time. Finally, pulsations in gas flow rates due to cylinder firings and the electrical noise typical of automobiles make it difficult to control and monitor the low voltage and current circuits associated with these devices.

The disclosed gas sensor is directed at solving one or more of the problems set forth above.

SUMMARY OF THE DISCLOSURE

In one aspect, the present disclosure is directed to a gas sensor. The gas sensor may include a plurality of substrate members, a first sensing electrode, and a second sensing electrode. The gas sensor may also include a first heater element associated with the first sensing electrode and being located on a first side of one of the plurality of substrate members, and a second heater element associated with the second sensing electrode and being located on a second opposing side of the one of the plurality of substrate members.

In another aspect, the present disclosure is directed to another gas sensor. This gas sensor may include a substrate member having a first surface and a second surface, a first sensing electrode, and a second sensing electrode. The gas sensor may also include only a single heater element associated with the first sensing electrode and being bonded to the first surface, and only a single heater element associated with the second sensing electrode and being bonded to the second surface.

In yet another aspect, the present disclosure is directed to a method of sensing the concentration of constituents in a flow of exhaust gases. The method may include generating a first heating zone, and measuring a first parameter at the first heating zone. The first parameter may be indicative of a concentration of a first constituent in the flow of exhaust gases. The method may further include generating a second heating zone isolated from the first heating zone by an insulative boundary layer, and measuring a second parameter at the second heating zone. The second parameter may be indicative of a concentration of a second constituent in the flow of exhaust gases.

DETAILED DESCRIPTION

Figure 1:
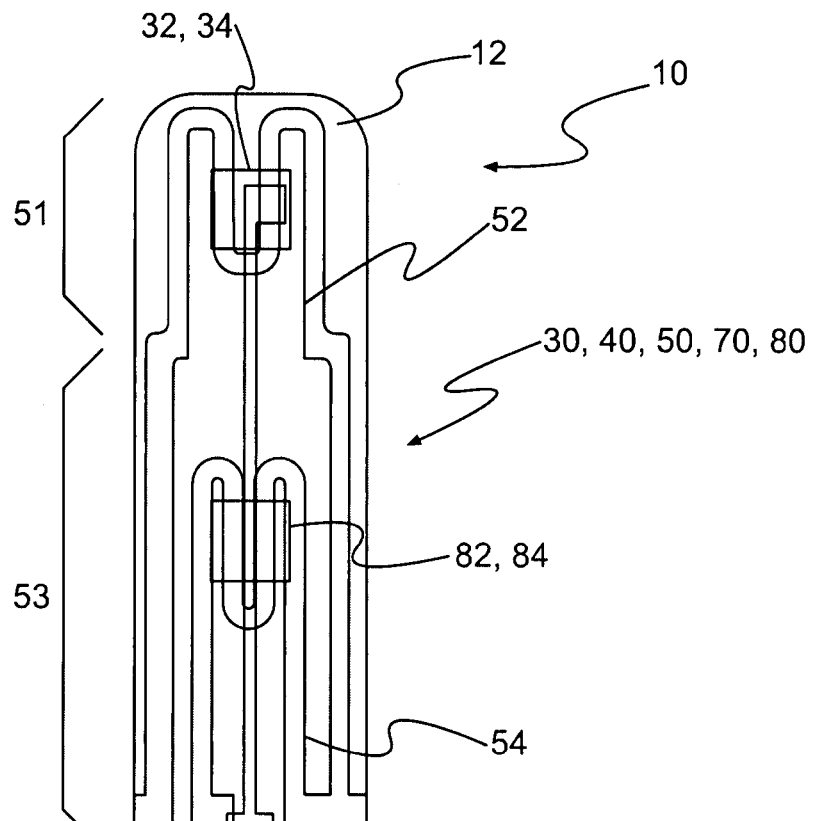
FIG. 1 is a schematic view illustration of an exemplary disclosed sensing assembly.

Referring to FIG. 1, the basic features of a sensor element 10 are illustrated. More specifically, sensor element 10 is depicted in a schematic view such that a plurality of individual layers 30, 40, 50, 70, and 80, used to make up sensor element 10, are shown to overlap as they would in a fully assembled sensor element 10. This view illustrates the relationship between features of sensor element 10.

In sensor element 10, an oxygen sensing electrode 32 may be positioned spatially near a first heater element 52 and on an outer face of sensor element 10 (i.e., on an outer face of layer 30, which may be the first of the two opposing outside layers of sensor element 10). Sensor element 10 may also include a reference electrode 34 positioned on an inner face of layer 30 in a substantially similar position as heater element 52 (i.e., reference electrode 34 may be substantially aligned with heater element 52 in a width and a length direction of sensor element 10). As a result, when viewed as in FIG. 1, oxygen sensing electrode 32 and reference electrode 34 may substantially overlap at a first end of layer 30 to form an oxygen sensor.

Similarly, a $NO_X$ sensing electrode 82 may be positioned spatially near a second heater element 54 on an outer face of sensor element 10 (i.e., on an outer face of layer 80, which may be the second of the two opposing outside layers of sensor element 10). A reference electrode 84 may be positioned on an inner face of layer 80 in a substantially similar position as heater element 54 (i.e., reference electrode 84 may be substantially aligned with heater element 54 in a width and a length direction of sensor element 10). As a result, when viewed as in FIG. 1, $NO_X$ sensing electrode 82 and reference electrode 84 may substantially overlap at a location spaced apart from the first end of sensor element 10 in a length direction to form a $NO_X$ sensor. In some embodiments, a $NO_X$ sensor that is insensitive to oxygen may be used. In such cases, reference electrode 34 may be omitted from sensor element 10. Other sensors such as hydrocarbon sensors and/or CO sensors may be substituted in the place of the sensors described herein.

Heater element 52 may heat oxygen sensing electrode 32 to a temperature range of about 500° C.-900° C. and, more preferably, to a temperature range of about 650° C.-750° C. to create a first temperature zone 51. In some specific embodiments, heater element 52 may heat first temperature zone 51, which may substantially encompass oxygen sensing electrode 32, to a temperature of about 700° C. Heater element 54 may heat $NO_X$ sensing electrode 82 to a temperature range of about 300° C.-600° C. and, more preferably, to a temperature range of about 450° C.-550° C. to create a second temperature zone 53. In some specific embodiments, heater element 54 may heat second temperature zone 53, which may substantially encompass $NO_X$ sensing electrode 82 to a temperature of about 500° C. It should be noted that, heater elements 52, 54 may additionally provide heat to a catalyst (not shown), thus further improving the function of the apparatus as a whole.

A coil length and/or cross-sectional area of heater element 52 may be different from a length and/or cross-sectional area of heater element 54, and this length and/or area difference may facilitate the different temperatures ranges of temperature zones 51 and 53 (i.e., the resistance associated with the different lengths and/or areas may contribute to the resulting temperature differences). In one embodiment, the resistance of a power lead combined with a resistance of a ground lead associated with one of the first and second heating elements may be about 25% less than a resistance of the heater element itself. Heater elements 52 and 54 may be designed to accommodate a supply of power in the range of about 9-24 volts and, more specifically, in the range of about 12-18 volts.

Heater elements 52, 54 may be located such that the resulting temperature zones 51, 53 may be substantially isolated from each other (i.e., such that one heating zone does not substantially affect a temperature of the other heating zone). That is, in addition to being located on opposing sides of layer 30, heater elements 52, 54 may also be spaced apart in a length direction of layer 30. Thus even though heater elements 52 and 54 may be substantially aligned in a width direction of layer 30, the spacing in the length direction may help to thermally isolate temperature zone 51 from temperature zone 53.

Each of layers 30, 40, 50, 70, and 80 may be initially produced from a green ceramic tape made using zirconia powder mixed with binders, solvents, and plasticizers into a slurry suitable for tape casting. A variety of ion-conductive ceramic materials are known in the art for constructing conductive portions of sensor element 10, as would be understood by one of ordinary skill in the art. In some embodiments it may be advantageous to add a non-conductive or insulating region to sensor element 10. A variety of insulative ceramic materials are also known in the art and could be used for constructing sensor element 10, as would be understood by one of ordinary skill in the art. Following production of the zirconia slurry, the slurry may be tape cast and dried prior to further manufacturing steps. Segments of the dried tape may be cut to approximate shape using techniques common in the art.

Figure 2:
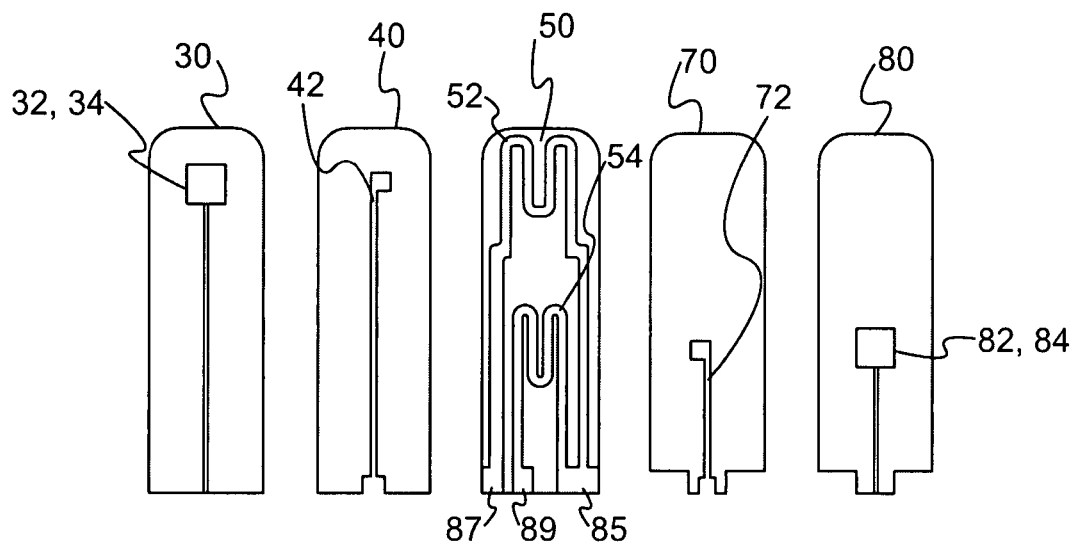
FIG. 2 is a disassembled view illustration of the sensing assembly of FIG. 1.

As illustrated in FIG. 2, layer 30 may be provided for placement of oxygen sensing electrode 32 and reference electrode 34. Oxygen sensing electrode 32 may be generally composed of platinum, but may not be printed onto layer 30 until after sensor element 10 of FIG. 1 has been assembled and sintered. Although oxygen sensing electrode 32 may be printed onto layer 30 prior to sintering in some circumstances, sintering of oxygen sensing electrode 32 may reduce its porosity, and hence, its sensitivity and effectiveness.

Layer 40 may be cut to include a channel 42 extending into sensor element 10 from one end thereof. Channel 42 may allow entry of a reference gas, which is typically air. The length and geometry of channel 42 may be varied widely within the scope of this disclosure. Layer 70 may also include a channel 72 extending into sensor element 10 from the same end thereof as channel 42. Channels 42, 72 may allow air to enter sensor element 10 to reach reference electrodes 34 and 84 placed on interior surfaces of layer 30 and layer 80, respectively. As with channel 42 provided in layer 40, channel 72 of layer 70 may be varied in size and geometry within the scope of this disclosure.

FIG. 2 further illustrates layer 50 adapted to include heater elements 52, 54 that produce first and second temperature zones 51, 53. Heater elements 52, 54 may be constructed to be independently-controlled, having distinct power sources; or to be controlled by the same power source and rendered capable of producing first and second temperature zones 51, 53 by varying the resistance of the individual heater elements 52, 54. Resistance may be varied in many ways, as understood by one of ordinary skill, in the art, including increasing the lengths of the heater elements 52, 54.

Heater elements 52, 54 may be connected to receive power in series or in parallel. Specifically, heater elements 52, 54 may be connected to each other at one end 85, while the other end 87, 89 of each heater element 52, 54 may be free. Thus, power could be supplied to each of the free ends 87, 89 and a ground connected to end 85 such that each heater element 52, 54 operates in parallel. In this configuration, in addition to adjusting a resistance of each heater element 52, 54 to control a temperature of the associated temperature zones 51, 53, a different level of power could be supplied to each free end. Alternatively, power could be supplied to only one of the free ends 87 or 89, while the other of the free ends may be grounded such that each heater elements 52, 54 operate in series. In the series configuration, temperature differences between the temperature zones 51, 53 could be controlled solely by varying a resistance of each heater element 52, 54.

Heater elements 52, 54 may be positioned to be near oxygen and $NO_X$ sensing electrodes 32, 82, on opposing faces of layer 50 such that layer 50 provides at least some insulation between temperature zones 51, 53. Heater elements 52, 54 may be screen printed and dried in an oven at about 80° C. for about 2 hours prior to assembly of sensor element 10. After screen-printing the electrodes, the green ceramic layers 30, 40, 50, 70, and 80 may be laminated together using a technique such as solvent bonding, heat lamination, or another technique known to one of ordinary skill in the art. In methods using heat lamination, the individual layers are pressed together using a lamination press. After lamination of the layers 30, 40, 50, 70, and 80, sensor element 10 may be cut to final shape using techniques known to those of ordinary skill in the art, and then may be ready for sintering.

The green laminated ceramic tape sensor element 10 may then be sintered for about two hours at about 1475° C. Following sintering, sensor element 10 may be coated with platinum for oxygen sensing electrode 32 on the side corresponding to the layer 30, as schematically illustrated in FIGS. 1 and 2. The opposing side of the sensor element 10 corresponding with layer 80 may be coated with a composite of $WO3/ZrO2$ to make up $NO_X$ sensing electrode 82. $NO_X$ sensing electrode 82 may be preferably placed on sensor element 10 after sintering to prevent high-temperature chemical reaction with zirconia in the green tape. After placement of the electrodes, sensor element 10 may be fired at a high temperature in the range of about 800° C.-1000° C. and, in some instances, in the range of about 850° C.-950° C. to promote good adhesion of oxygen sensing electrode 32 and $NO_X$ sensing electrode 82 to the exterior of the sensor element 10.

In some embodiments, oxygen and $NO_X$ sensing electrodes 32, 82 may be mixed potential sensors constructed using a semi-conductive oxide material. In some specific embodiments, the semi-conductive oxide material may include at least one of the following: $WO_3$, $Cr_2O_3$, $Mn_2O_3$, $Fe_2O_3$, $TiO_2$, and $CO_3O_4$. In other embodiments, a multi-component oxide material may be used such as, for example, a spinel or perovskite. In some specific embodiments, the multi-component oxide material may be at least one of the following: $NiCr_2O_4$, $ZnFe_2O_3$, $CrMn_2O_3$, $LaSrMnO_3$, $LaSrCrO_3$, and $LaSrFeO_3$.

One of ordinary skill in the art would understand that the number and configuration of the layers 30, 40, 50, 70, and 80 used to construct sensor element 10 could be widely varied within the scope of this disclosure. Specifically, oxygen and $NO_X$ sensing electrodes 32, 82 and/or heater elements 52, 54 could be placed in a variety of locations, including on the same surface of individual layers. Further, channels 42, 72 could be embossed or partially etched from a layer instead of being cut completely through. Other variations, including variations of electrode material, shape, and in some instances, placement could be made within the scope of the invention by one of ordinary skill in the art.

Figure 3:
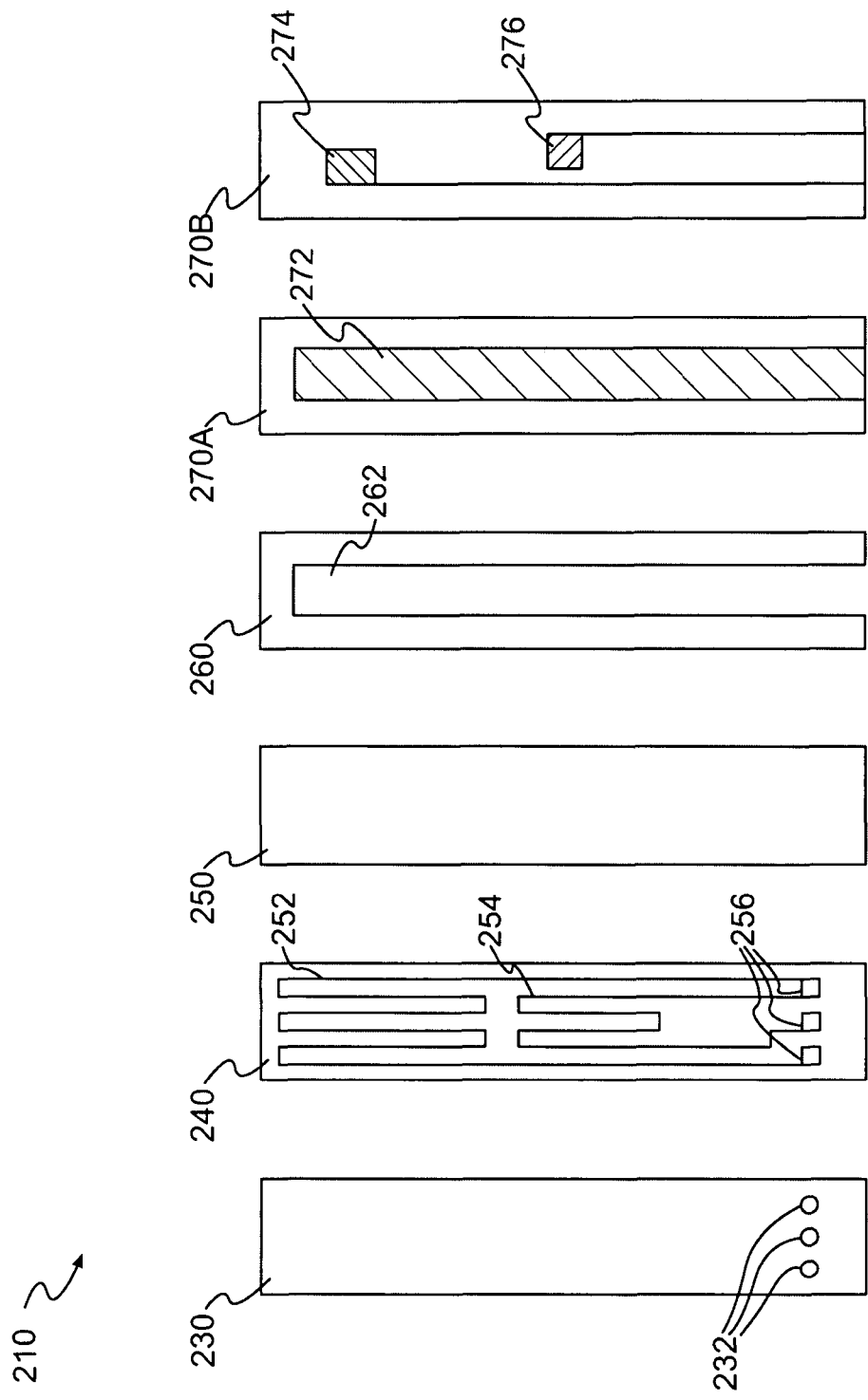
FIG. 3 is a disassembled view illustration of another sensing assembly.

FIG. 3 illustrates the individual layers of another sensor element 210. This embodiment may be assembled in a similar manner to that described with reference to FIGS. 1-2 discussed in greater detail above. Sensor element 210 may include an optional first layer 230. Layer 230 may include one or more through holes 232 to allow access to a plurality of heater elements 252, 254 located on a second layer 240. As described above, heater elements 252, 254 may be disposed on the same face of layer 230 or, alternatively, on opposing faces of layer 230. Layer 240 may be spaced from a channel layer 260 by an optional and electrically insulative layer 250. Channel layer 260 may include a channel 262 to allow entry of air being directed to a reference electrode 272 found on an interior face of layer 270. An oxygen sensing electrode 274 and a $NO_X$ sensing electrode 276 may be placed, as instructed above with reference to the embodiment of FIGS. 1-2, on an exterior face of the layer 270.

Figure 4:
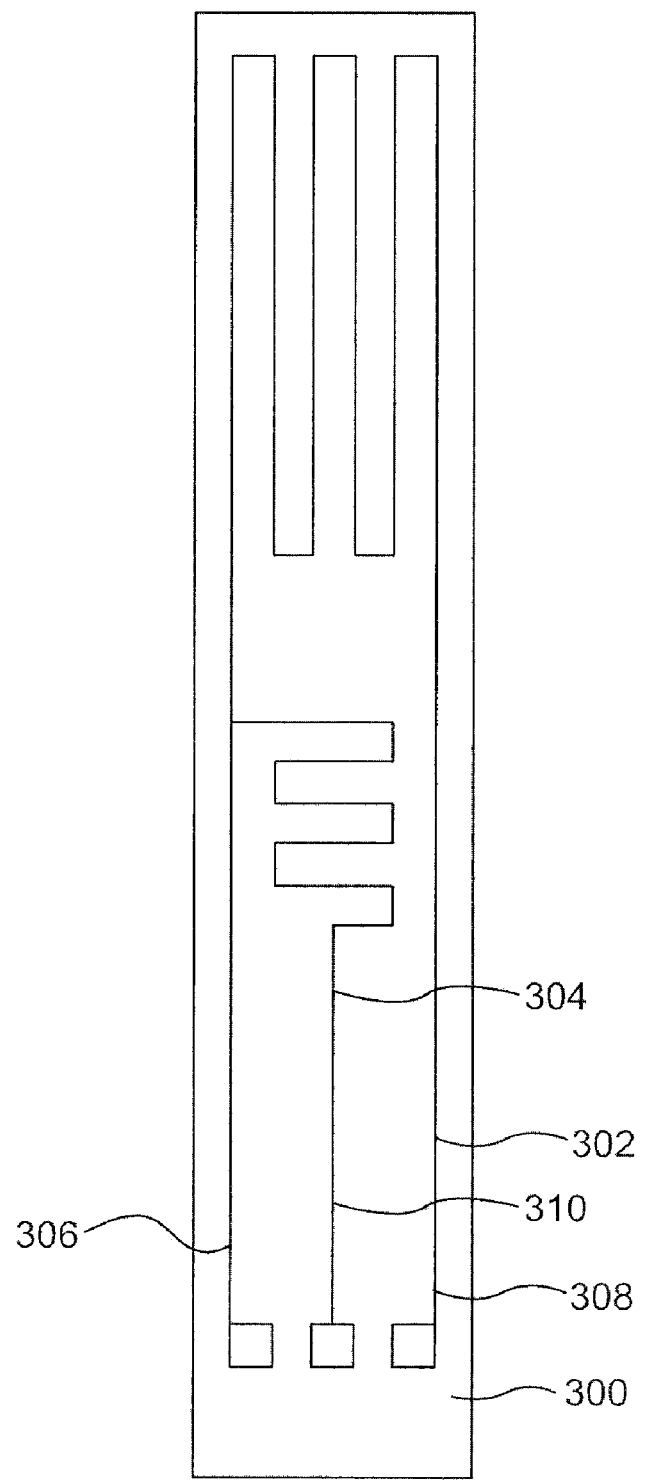
FIG. 4 is a schematic view illustration of an exemplary heater layer for the disclosed sensing assemblies of FIGS. 1 and 3.

FIG. 4 illustrates an alternative heater layer 300. In this heater layer, a first and a second heater element 302, 304 may share a common ground lead 306. That is, each of heater elements 302, 304 may receive power via separate power leads 308, 310, but terminate at ground lead 306. In addition, as can be seen in FIG. 4, heater element 304 may be oriented substantially orthogonal to heater element 302 (i.e., the coil direction of heater element 304 may be about perpendicular to the coil direction of heater element 302). This design may facilitate a more compact sensing element.

INDUSTRIAL APPLICABILITY

The presently disclosed sensing elements may be used as both an oxygen sensor and a $NO_X$ sensor, as it includes two distinct temperature zones. Specifically, one of the temperature zones may be associated with an oxygen sensor, while a second of the temperature zones may be associated with a mixed potential $NO_X$ sensor. The sensing elements of the present disclosure may improve overall system performance by miniaturizing the ceramic sensing element and including two sensing electrochemical cells. The sensing elements of the present disclosure additionally include two metallic patterns that function as "heater elements" to heat separate and isolated areas of the ceramic structure when a voltage and current are applied to contact points of the patterns.

By incorporating these heater elements into the ceramic structure of the sensor element, the heat transfer rate to the sensing electrodes is increased. An increased heat transfer rate provides more rapid light off times for the sensor components of the sensor element. In addition to the above, thermal stresses due to rapid changes in temperature are minimized by optimization of the heater design pattern and the construction of the multilayer ceramic package. These features may result in improved lifetime performance and reliability of the sensor apparatus.

It will be apparent to those skilled in the art that various modifications and variations can be made to the sensing element. Other embodiments will be apparent to those skilled in the art from consideration of the specification and practice of the disclosed sensing element. It is intended that the specification and examples be considered as exemplary only, with a true scope being indicated by the following claims and their equivalents.

What is claimed is:

1. A gas sensor, comprising:
 a plurality of substrate members;
 a first sensing electrode;
 a second sensing electrode;
 a first heater element associated with the first sensing electrode and being attached to a first side of one of the plurality of substrate members; and
 a second heater element associated with the second sensing electrode and being attached to a second opposing side of the one of the plurality of substrate members, wherein the one of the plurality of substrate members has a first dimension greater than a second dimension, and the second heater element is spaced apart from the first heater element in a first direction corresponding with the first dimension.

2. The gas sensor of claim 1, wherein the second heater element is substantially aligned with the first heater element in a second direction corresponding with the second dimension.

3. The gas sensor of claim 1, wherein the first heater element includes a coil having a first length and the second heater element includes a coil having a second length the first length being substantially different from the second length.

4. The gas sensor of claim 1, wherein the first heater element is aligned along a first direction and the second heater element is aligned along a second direction, the first direction being substantially orthogonal to the second direction.

5. The gas sensor of claim 1, wherein the first and second heater elements share a common ground connection.

6. The gas sensor of claim 1, wherein the first and second heater elements are connected in series.

7. The gas sensor of claim 1, wherein at least one of the first and second heater elements are fabricated prior to bonding with the one of the plurality of substrate members.

8. The gas sensor of claim 1, wherein the first heater element is the only heater element on the first side of the one of the plurality of substrate members and the second heater element is the only heater element on the second side of the one of the plurality of substrate members.

9. The gas sensor of claim 1, wherein the first and second heater elements are designed to accommodate a supply of power in the range of about 9-24 volts.

10. The gas sensor of claim 1, wherein:
 the first sensing electrode is located on a second of the plurality of substrate members in opposition to the first heater element; and
 the second sensing electrode is located on a third of the plurality of substrate members in opposition to the second heater element.

11. The gas sensor of claim 10, wherein a fourth substrate member of the plurality of substrate members is located between the one of the plurality of substrate members and one of the second and third of the plurality of substrate members, the fourth of the plurality of substrate members being in fluid communication with a flow of exhaust gases.

12. The gas sensor of claim 1, wherein:
 the first heater element produces a first heating zone at a first temperature during operation;
 the second heater element produces a second heating zone at a second temperature during operation; and
 the first heater element and the first heating zone are substantially isolated from the second heater element and second heating zone during operation.

13. The gas sensor of claim 12, wherein the first temperature is in the range of about 300-600° C. and the second temperature is in the range of about 500-900° C.

14. The gas sensor of claim 1, wherein:
 the first heater element includes a first coil and a first power lead connected to the first coil;
 the second heater element includes a second coil and a second power lead connected to the second coil; and
 the first power lead has a length substantially longer than a length of the second power lead.

15. The gas sensor of claim 14, wherein the length of the first power lead is about two times the length of the second power lead.

16. The gas sensor of claim 14, wherein the first heater element further includes a ground lead and the resistance of the first power lead combined with the resistance of the ground lead is about 25% less than a resistance of the first heater element.

17. The gas sensor of claim 16, wherein the first and second heater elements are designed to accommodate a power supply more specifically in the range of about 12-18 volts.

18. A gas sensor, comprising:
 a substrate member having a first surface and a second surface opposite the first surface;
 a first sensing electrode;
 a second sensing electrode
 only a single heater element associated with the first sensing electrode and being bonded to the first surface; and
 only a single heater element associated with the second sensing electrode and being bonded to the second surface, wherein the substrate member has a first dimension greater than a second dimension, and the single heater element bonded to the second surface is spaced apart from the single heater element bonded to the first surface in a first direction corresponding with the first dimension.

19. The gas sensor of claim 18, wherein the single heater element bonded to the first surface is connected in series with the single heater element bonded to the second surface.

20. The gas sensor of claim 18, wherein at least one of the single heater element bonded to the first surface and the single heater element bonded to the second surface is fabricated prior to bonding with the substrate member.

21. The gas sensor of claim 18, wherein:
 the first heater element produces a first heating zone at a first temperature during operation;
 the second heater element produces a second heating zone at a second temperature during operation; and
 the first heater element and the first heating zone are substantially isolated from the second heater element and second heating zone during operation.

* * * * *